United States Patent [19]

Sobel et al.

[11] Patent Number: 5,165,217
[45] Date of Patent: Nov. 24, 1992

[54] ONE PIECE CHANNEL SUTURE PACKAGES

[75] Inventors: Martin Sobel, Flemington; Stephen George, Wayne; Anthony Esteves, Somerville, all of N.J.; Robert J. Cerwin, Pipersville, Pa.; Marvin Alpern, Glen Ridge; Robert A. Daniele, Flemington, both of N.J.

[73] Assignee: Ethicon, Inc., Somerville, N.J.

[21] Appl. No.: 730,157

[22] Filed: Jul. 15, 1991

Related U.S. Application Data

[62] Division of Ser. No. 563,236, Aug. 6, 1990, Pat. No. 5,056,658, which is a division of Ser. No. 406,223, Sep. 12, 1989, Pat. No. 4,967,902.

[51] Int. Cl.⁵ .......................... B65B 63/04; B65B 31/02
[52] U.S. Cl. ......................................... 53/430; 53/432; 53/491; 606/222; 242/159
[58] Field of Search ............... 606/222; 242/159, 171; 53/116, 409, 430, 432, 491; 206/63.3, 380

[56] References Cited

U.S. PATENT DOCUMENTS

| | | | |
|---|---|---|---|
| 1,821,354 | 9/1931 | Meyer | 242/159 |
| 2,713,938 | 7/1955 | Snyder | 53/491 X |
| 2,741,009 | 4/1956 | Slayter et al. | 53/116 |
| 3,167,895 | 2/1965 | Egler et al. | 53/430 X |
| 3,490,192 | 1/1970 | Regan | 53/432 X |
| 3,726,057 | 4/1973 | Kemble | 53/432 X |
| 3,759,376 | 9/1973 | Lisowski | 53/430 X |
| 3,972,418 | 8/1976 | Schuler et al. | 206/63.3 |
| 4,424,898 | 1/1984 | Thyen et al. | 206/63.3 |
| 4,903,826 | 2/1990 | Pearce | 242/171 X |

FOREIGN PATENT DOCUMENTS 1201094  2/1986  Canada .............................. 606/222

Primary Examiner—John Sipos
Assistant Examiner—Linda B. Johnson
Attorney, Agent, or Firm—Paul A. Coletti

[57] ABSTRACT

A one piece needle and suture holder is described in which a rounded channel is formed for retention of the suture. One end of the suture exits the channel toward the interior of the channel and is attached to a needle located in a needle holder in the interior of the channel. The channel is formed with an open side, to which are attached a plurality of hinged doors. After the suture is wound in the open channel, the doors are folded over the open side of the channel and are locked in place to retain the suture within the channel. In an alternative embodiment a paper cover is utilized to complete the enclosing channel. To afford ease of winding the suture the bottom of the channel is preforated for the application of a vacuum to the channel during suture winding. Also disclosed is a needle park for retaining the needle in the center of the package. In a preferred embodiment the needle park is backed by a relief flap to enable the needle to be conveniently grasped by a forceps during removal of the needle and suture.

2 Claims, 5 Drawing Sheets

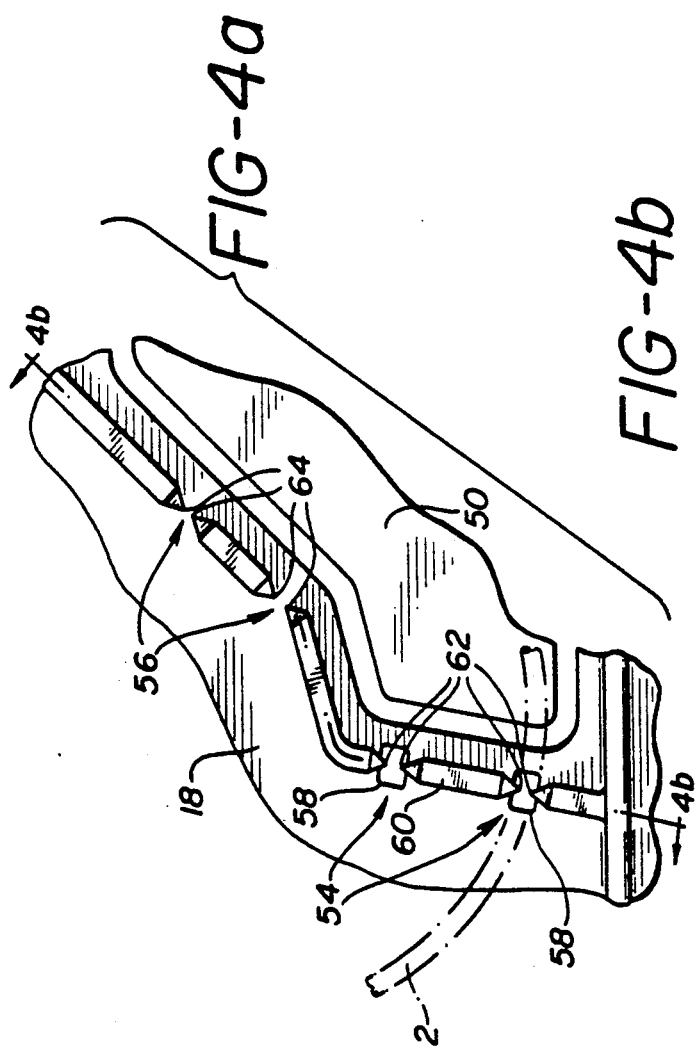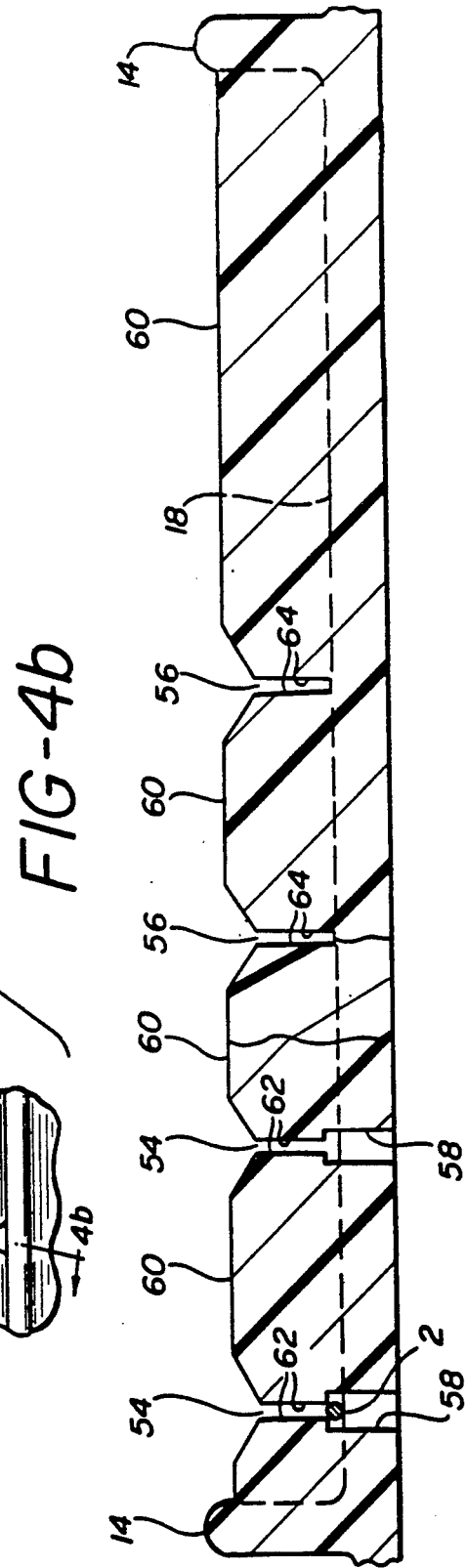

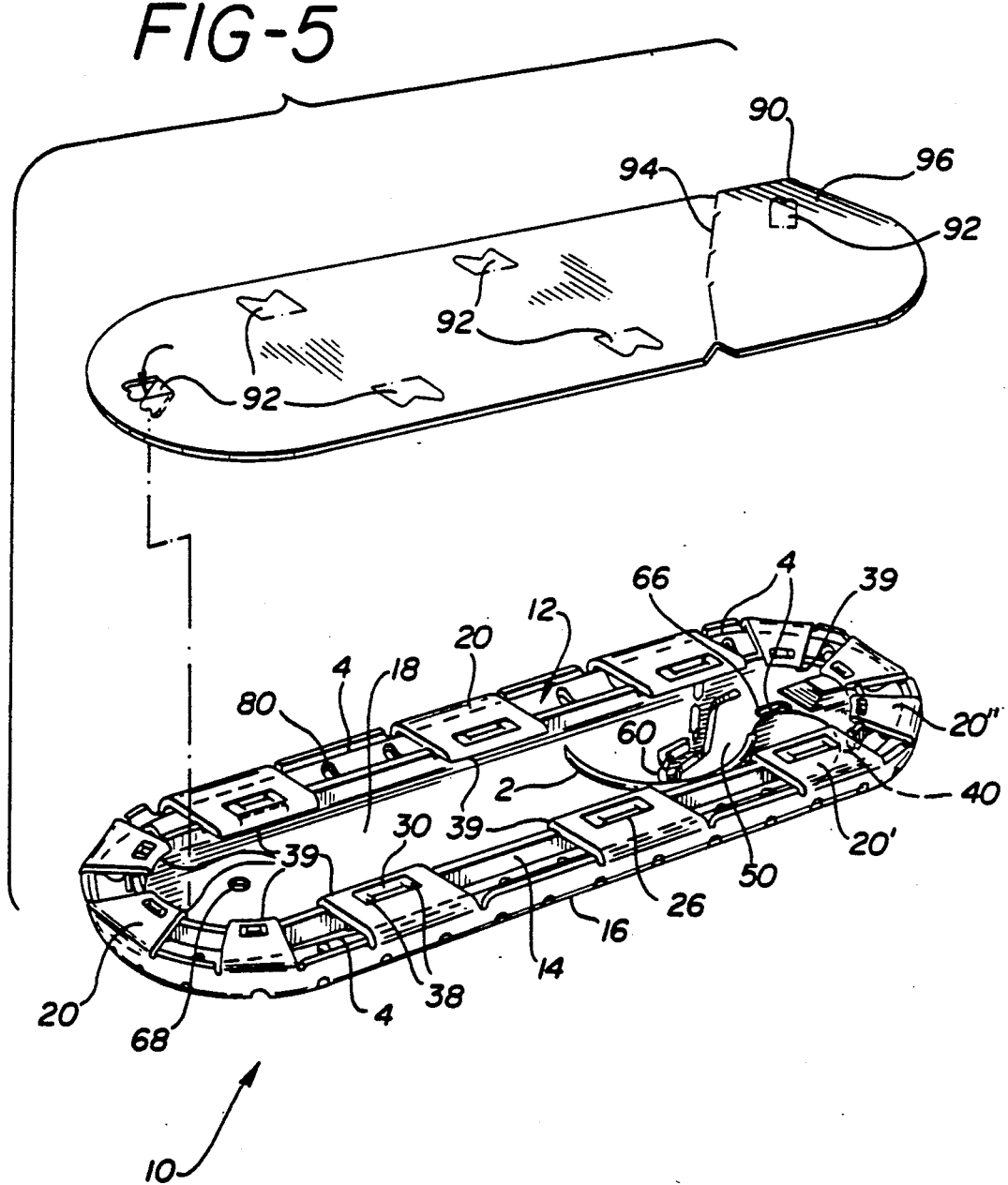

5,165,217

ONE PIECE CHANNEL SUTURE PACKAGES

This is a division of application Ser. No. 563,236, filed Aug. 6, 1990, now U.S. Pat. No. 5,056,658, which is a division of Ser. No. 406,223, filed Sep. 12, 1989, now U.S. Pat. No. 4,967,902.

This invention relates to holders for needles and, in particular, to holders and packages formed of a single molded piece and forming a channel for the retention and delivery of sutures containing attached needles.

In the packaging of surgical needles including surgical needles to which there are attached sutures, it is important that the needle and its attached suture be easily removable from the package in one smooth motion. When the needle is grasped by a forceps and pulled, the needle should easily release from the package, and the suture should withdraw from the package smoothly without binding or snagging in the package, and without becoming entangled. Also, suture materials, particularly monofilaments such as catgut, polydioxanone and the like, especially the heavier deniers, are known to take a set during storage; i.e., they tend to have a "memory" causing them to retain the shape of their position in the package after removal from the package. Hence the package should be designed so that any tight bends or curves required in order to package the suture be eliminated.

It is further desirable for suture packages to be economical to manufacture in volume quantities. A manufacturing process directed toward this end is one in which the suture package is formed of two interlocking molded, stamped, or thermoformed polymeric members. Packages made in such a process enable the formation of projections useful for winding and capturing the suture in channels designed for that purpose. These packages also enable the maintenance of fine tolerances necessary in the execution of a precision design.

Molded, stamped or thermoformed polymeric suture packages as described above are shown in U.S. Pat. Nos. 3,972,418 (Schuler et al.); 4,424,898 (Thyen et al.); 4,549,649 (Roshdy); 4,699,271 (Lincoln et al.) and in U.S. patent application Ser. No. 236,057, entitled "OVAL WRAP SUTURE PACKAGE" and filed on Aug. 24, 1988, now U.S. Pat. No. 4,961,498. The latter application describes a two-piece oval suture package in which is formed a channel for winding and retention of the suture. The channel is fully formed when an upper piece of the package mates with the lower piece of the package to fully enclose the suture wound in the channel. The needle which is attached at one end of the suture is retained in a needle part formed in the center of the oval channel, with the attached suture passing through a vent opening in the inner wall of the channel.

This two-piece package requires the molding or stamping of two pieces to form the package, which is relatively costly and requires the assembly of the two pieces in association with the winding of the suture in the package. It would be desirable to reduce the cost of such a package by providing a package with an enclosed channel through the use of a single package piece. Such a one-piece package would simplify the molding and handling of the packages and would reduce the product cost.

In accordance with the principles of the present invention, a one piece needle and suture holder is described in which an oval-shaped channel is formed for retention of the suture. One end of the suture exits the oval channel toward the center of the oval and is attached to a needle located in the center of the oval. The oval channel includes gently rounded end sections, eliminating any tight bends or curves which would induce undesirable suture "memory". The oval channel is formed with an open side, to which are attached a plurality of hinged doors. After the suture is wound in the open channel, the doors are folded over the open side of the channel and are locked in place to retain the suture within the channel. The illustrated embodiments describe two techniques for locking the doors, and an alternate embodiment utilizes a paper cover to complete the enclosing channel. To afford ease of winding the suture the bottom of the channel is perforated for the application of a vacuum to the channel during suture winding. The vacuum will draw the suture into the channel and hold the suture in place until the channel is enclosed by the doors or the paper cover. Also disclosed is a needle park for retaining the needle in the center of the package. In a preferred embodiment the needle park is backed by a relief flap to enable the needle to be conveniently grasped by a forceps.

IN THE DRAWINGS

Figure 1:
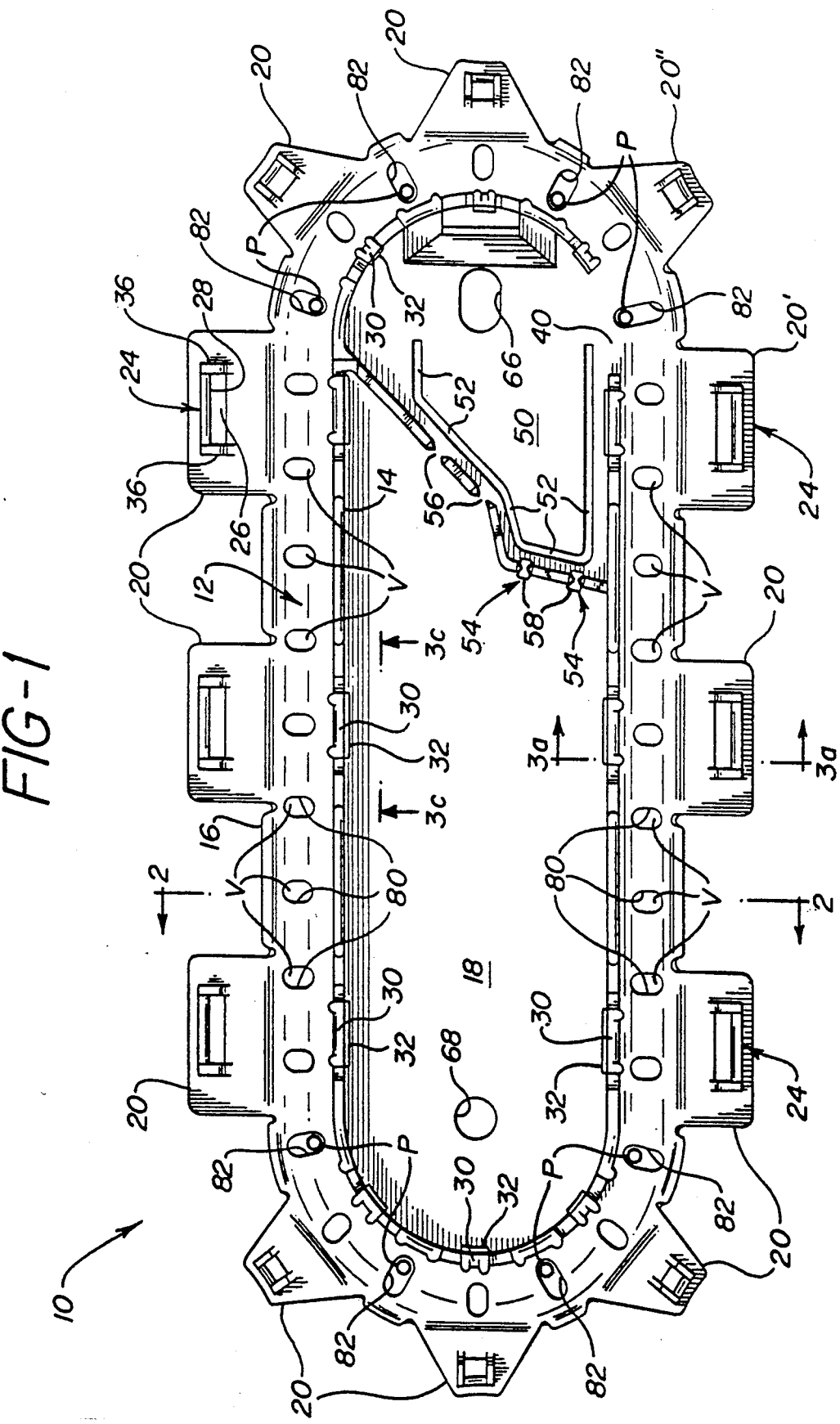
FIG. 1 illustrates a plan view of a one piece suture package constructed in accordance with the principles of the present invention.
Figure 2:
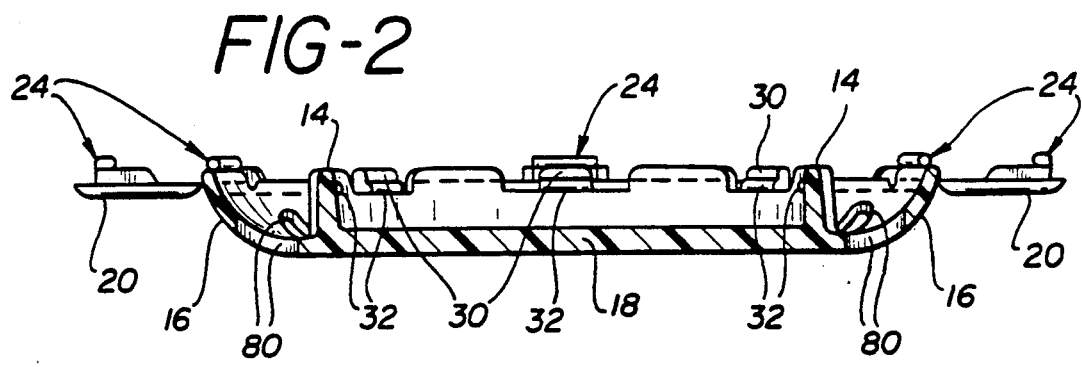
FIG. 2 is a cross-sectional view of the suture package of FIG. 1.
Figure 3A:
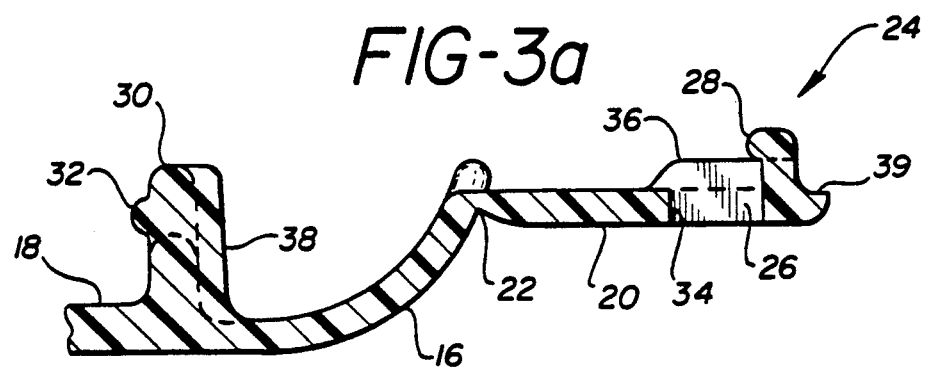
Figure 3B:
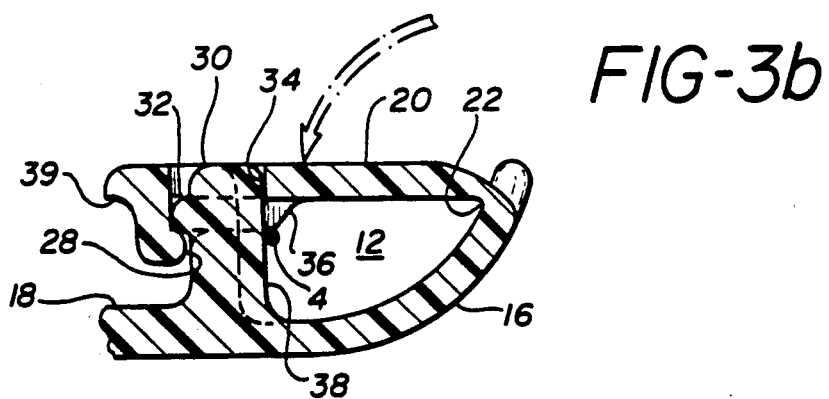
Figure 3C:
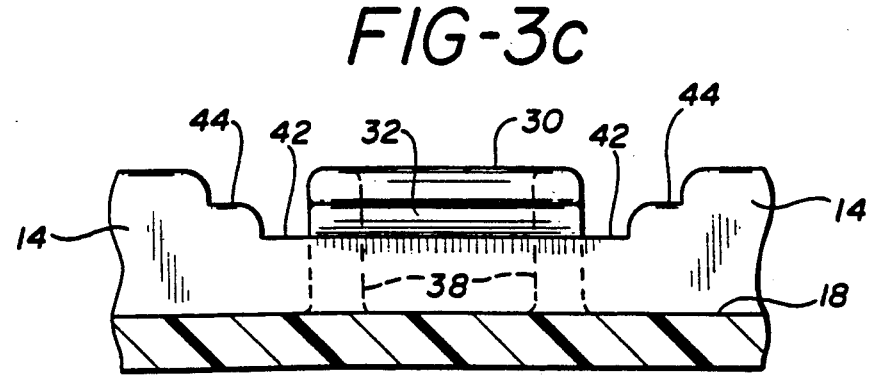
Figure 6:
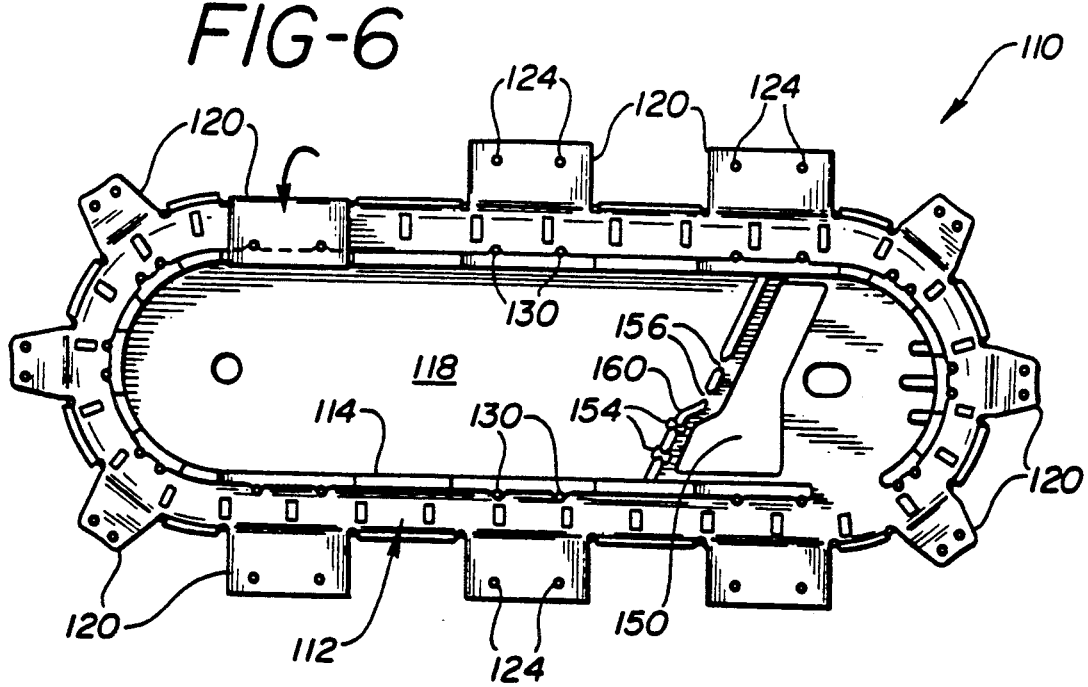
Figure 7:
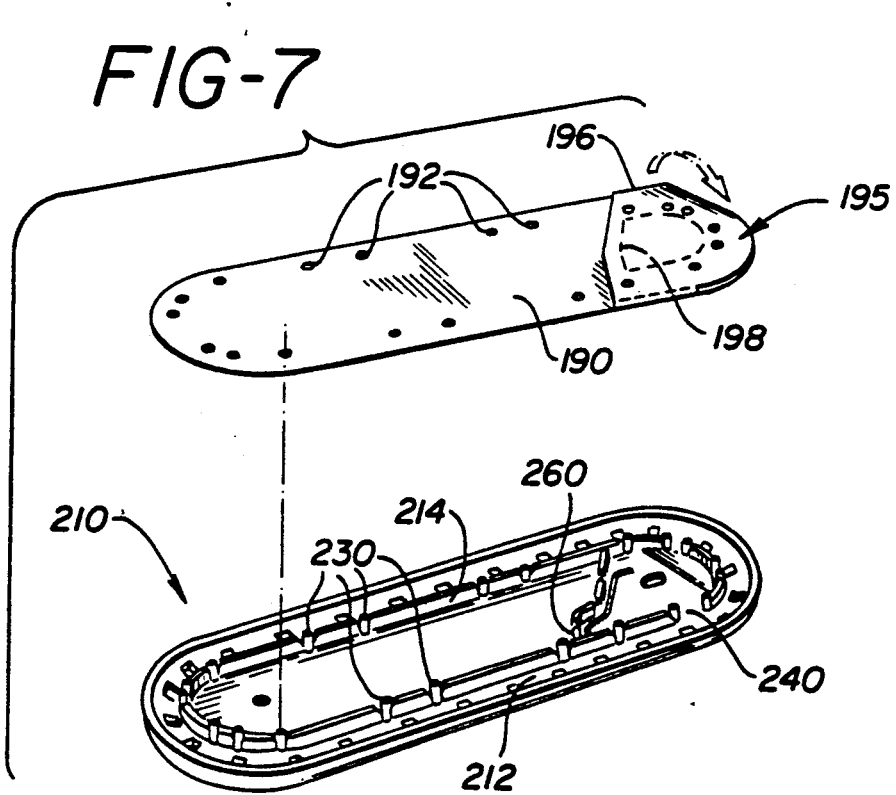

FIGS. 3a, 3b, and 3c are detailed views of the hinged doors of the suture package of FIGS. 1 and 2;

FIGS. 4a and 4b are partial plan and cross-sectional views of the needle holder of the suture package of FIG. 1;

FIG. 5 is an assembly drawing of the suture package of FIG. 1 with a paper cover;

FIG. 6 is a plan view of a suture package of the present invention utilizing an alternate locking mechanism for the channel doors; and FIG. 7 illustrates a further embodiment of a suture package of the present invention utilizing a paper cover to enclose the suture winding channel.

Referring first to FIGS. 1 and 2, a one piece suture package 10 of the present invention is shown in plan and cross-sectional views. The package may be formed of any surgically compatible polymeric materials, such as polyester plastic, polyethylene, polyvinyl chloride (PVC) polypropylene, or polystyrene. The package includes a central floor area 18 which is surrounded by an outer oval channel 12 having two opposing straight sections connected by two semicircular end sections. The channel is defined by an inner wall 14 which extends upwardly from the floor area. Portions of the door locking means are formed at intervals about the inner wall 14. The bottom and outer periphery of the channel 12 is defined by a curved section wall 14 at the level of the floor 18 and curves upwardly to approximately the elevation of the inner wall 14. Attached at the outer periphery of the curved section 16 are a plurality of hinged doors 20. The doors are hinged at an elevation which is slightly below the uppermost elevation of the outer periphery of the curved section and the inner wall so that, when the doors are folded over the channel and latched in place, the upper surfaces of the doors will align with the upper elevation of the outer periphery and inner wall. Formed in each door is a portion of the door locking means, including a latch opening 26 bounded by a door latch projection 28 and two fins 36, which are described in further detail below.

Located inside the oval channel is a needle park including undercut and rigid needle holders 54 and 56, which will be described in further detail below. Adjacent the needle park is a relief flap 50 defined by a cutout 52. A portion of the inner wall 14 is eliminated in the vicinity of the needle park to form a vent 40 in the channel wall through which the suture of the needle accesses the channel 12 between doors 20' and 20". The bottom of the channel 12 formed by the curved section 16 is periodically perforated by holes 80 and 82 around the circumference of the channel.

FIG. 3a is a partial cross-sectional view of the package of FIG. 1 showing in enlargement a hinged door 20 and the channel 12. The hinge 22 of the door 20 is attached to the outer periphery of the channel at an elevation which is just below the uppermost elevation of the channel on either side of the hinge so that the door will be flush with the top of the channel when it is closed. The door locking means 24 includes a door latch opening 26 and a door latch projection 28. An overhand 39 is formed at the edge of the door. A fin 36 is located at each end of the door latch opening 26.

Referring concurrently to FIG. 3c, a latch post 30 is formed in the inner wall 14 opposite the hinged door 20. A pair of standoffs 38 are formed along the inner wall at either end of the latch post location as shown also in FIG. 1. Extending from the latch post 30 toward the inside of the package (i.e., over the floor 18) is a latch post projection 32.

When the door 20 is closed and latched to retain a suture within the channel 20 it has the cross-sectional appearance as shown in FIG. 3b. The top of the latch post 30 engages the door latch opening 26 and the door latch projection 28 hooks around the latch post projection 32 to lock the door in the closed position. The door is prevented from unlatching in the presence of lateral compression by the abutment of the edge 34 of the opening 26 against the edges of the standoffs 38, which prevents unhooking of the two projections. When the door is closed the sides of the door rest on the edges 44, shown in FIG. 3c, locating the upper surface of the door flush with the top of the inner wall 14. The fins 36 at either end of the opening 26 engage the openings 42 at either end of the latch post 30. The fins 36 and the standoffs 38 serve to prevent the suture from binding or becoming entrapped in the door locking means. As FIG. 3b illustrates, the curved fins 36 and the standoffs 38 cause the suture to be located away from and to bridge the engaged door opening and latch post, preventing the suture from becoming caught between these two members, either during closure of the door or during withdrawal of the suture from the channel.

Referring to FIGS. 4a and 4b the needle park of the package of FIG. 1 is shown in greater detail. The needle park comprises a wall 60 extending upward from the central floor 18 of the package. The wall 60 is interrupted periodically by openings and the wall ends are tapered at the openings as shown at 62 and 64 to form needle holders 56 and 54. The needle holder 56 has the tapered wall ends secured to the underlying floor of the package, enabling only minimal movement and flexing of the tapered ends when a needle is inserted between them. This relatively rigid needle holder 56 will thus retain only a needle of a gauge which is matched fairly closely to the dimension of the opening. By comparison the package floor beneath the needle holder 54 has been undercut by removal of the floor area indicated at 58, which enables the tapered ends of the overlying needle holder to flex and bend somewhat when a needle is inserted in the wall opening. Thus the undercut needle holder 54 can accommodate a relatively wider range of needle gauges as compared with the rigid needle holder 56. Furthermore, the undercut needle holder 54 is undercut upward a short dimension from the floor surface, which causes a needle 2 to be securely retained in the undercut space below the tapered wall ends and above the surface of the package floor, as illustrated in FIG. 4b.

FIGS. 1 and 4b show that the needle park contains two rigid needle holders and two undercut needle holders. This permits the package 10 to hold either a suture with a needle at one end, or a suture with needles attached at both ends, with a choice of needle holders for either type of suture. With the choice of two types of needle holders, the package can accommodate a wide range of needle gauges.

Referring to FIG. 5, an assembled package 10 with a needle 2 and suture 4 is shown with a paper cover 90. The package is easily assembled by placing the package 10 on an assembly platform with a number of upwardly extending pins. Two of the pins are aligned to extend upward through holes 66 and 68 in the center of the package to retain the package in its assembly position on the platform. Eight other pins extend upward and are aligned to pass through the holes 82 of the channel (see FIG. 1). The platform is open beneath the remaining channel holes 80 and a vacuum source below the platform draws air through the holes 80. With the package so emplaced, the needle 2 is located in the needle holder as shown in the drawing, and the suture 4 is looped above the pin extending through hole 66 then downward through the vent 40 and into the channel 12. The suture is then wound in a clockwise direction around the pins which extend through the channel holes 82. It may be seen in FIG. 1 that the holes 82 extend inward toward the center of the package by a greater dimension than the holes 80. This allows location of the extending pins P close to the inner wall 14. When the suture is wound around the pins P and the pins P then are withdrawn from the holes, the suture will be loosely positioned in the center of the channel 12, since the pins serve to keep the suture away from the inner wall of the channel during winding by the dimension of the thickness of the pins. As the suture is wound around the pins the flow of vacuum V through the holes 80 will draw the suture down into the channel. When the end, or "tail" of the suture is reached, the flow of air will likewise draw the tail of the suture into the channel. With the suture completely wound in the channel the door are folded closed and latched to the latch posts of the inner channel wall. The pins are then withdrawn from the holes 66, 68, and 82.

The paper cover 90 is then placed over the top of the package to fully protect the suture and needle from any further contact during final assembly of the package. The cover 90 includes a scored tear line 94 along which the cover will preferentially tear when it is grasped at the tear corner 96 for opening. The cover 90 also includes a plurality of perforated push-out tabs 92. These tabs are located so as to be in alignment with ones of the closed doors 20. When the tabs are pressed downward the outer edges of the tabs snap under the overhanging edges 39 of the doors with which they are aligned, which retains the cover in place on the package 10. The fully enclosed suture package is then ready for final overwrap packaging, which generally comprises hermetically sealing the package in a foil overwrap.

When the package is to be opened the user grasps the tear corner 96 of the package and tears the overwrap and cover downward, causing the cover 90 to open along the scored tear line 94. This reveals that portion of the package to the right of the needle holder wall 60, with the point of the needle still protected by the cover to the left of the holder. The user then grasps the needle with a forceps. Since the needle is resting flush with the floor of the package, making it difficult to securely grasp the needle with the tip of the forceps, the relief flap 50 is provided. As the user presses the tip of the forceps against the relief flap the flap will give way and bend away from the needle, thereby enabling the user to pass the tip of the forceps beyond the needle. The needle may then be securely grasped in the tip of the forceps and removed from the needle holder.

Moreover, when the package is enclosed in a foil overwrap, the silver of the foil which backs the package behind the needle can blend with the silvery needle, causing the needle to be difficult to distinguish from this reflective background. The relief flap 50 obviates this problem by presenting a contrasting background behind the needle. The polymeric package can be tinted or colored a milky white or some other contrasting color, which will highlight the needle in front of the relief flap. The flap also covers the foil overwrap located behind the flap. This contrasting background thus makes it easier to clearly see fine gauge needles in the package.

FIG. 5 shows a ramp 67 formed to the right of the relief flap location. The ramp 67 is also shown in FIG. 1. The purpose of the ramp 67 is to guide the needle barrel up and out of the package during withdrawal, without snagging on the inner wall 14 of the channel at the oval end of the package.

In a conventional figure-8 wound suture package, the suture is looped from its point of attachment at the barrel of the needle back toward the point of the needle, where the figure-8 wind is formed. This configuration can cause the needle tip to catch on a loop of the suture and damage the suture. However, in the package of the present invention it may be seen that the suture is looped to the right from the needle barrel, around the hole 66 and down through the vent 40. This winding pattern keeps the suture removed to the right of the needle and the needle point. As the needle is lifted from the needle holder and the right of and away from the needle point and any possible damage.

FIG. 6 is a plan view of an alternate embodiment of the present invention. The package 110 of FIG. 6 is similar to the embodiment of FIG. 1, containing a central floor 118, an inner channel wall 114, an oval channel 112, and hinged doors 120. In this embodiment the door locking means includes a plurality of posts 130 located around the outer surface of the wall 114 in alignment with the doors 120. The posts 130 are offset from the surface of the wall 114 to provide standoffs for the suture from the wall 114. The door locking means also includes a pair of holes 124 formed in each door 120. When the hinged doors are closed the posts 130 mate in the holes 124 of the doors in a force fit to hold the doors closed. The posts 130 can alternatively by sized to extend through the doors, enabling the tips of the posts to be swaged to secure the doors in their closed position.

Like the embodiment of FIG. 1, the package 110 includes a needle park including rigid and undercut needle holders 156 and 154 formed in a needle holder wall 160. Instead of a relief flap, the package 110 has a relief opening 150 formed in the floor of the package adjacent the needle park. A user can securely grasp a needle for withdrawal by pinching the needle in the tip of a forceps with the forceps tip extended into the relief opening 150. In this embodiment a contrasting overwrap background would preferably be located behind the relief opening so that the silvery needle would be easily seen by the user.

FIG. 7 illustrates a further embodiment of the present invention in which the open suture winding channel is enclosed by a paper cover 190. The package 210 of this embodiment is similar to that of FIG. 6 with a channel 212 and a plurality of posts 230 extending upwardly from the inner wall of the channel, but this embodiment contains no hinged doors. After the needle is placed in the needle holder and the suture wound in the channel 212, a paper cover 190 is placed over the open package with holes 192 of the cover aligned with and engaging the posts 230. The ends of the posts which extend through the cover are then softened or swaged to hold the cover in place. The paper cover further includes a cover flap 195 overlying the needle position of the package. The cover flap is hinged to the cover 190 at 194. When the package and its overwrap are opened by tearing downward from the corner 196, the hinged cover flap 195 swings downward at its hinge to reveal a cutout area 198 of the underlying cover. The needle and suture may be accessed and withdrawn from the package through this cutout area 198 while the channel 212 remains completely enclosed by the paper cover 190.

What is claimed is:

1. A method for winding sutures in a suture package, said suture package having:
   a flat central area;
   a winding channel surrounding said central area containing an outer circumference and an inner wall, said winding channel having a base in spaced apart relation to said flat central area and containing a plurality of holes in said base;
   a portion of said holes configured for the placement of pins and a portion of said holes configured for applying vacuum pressure; and
   a plurality of flap portions placed in spaced apart relation along said outer circumference of said winding channel, said method comprising:
   placing a plurality of pins in said holes configured for pin placement;
   applying a vacuum force to said winding channel within said holes configured for vacuum pressure;
   winding a suture within said channel about said pins so that said suture lies in spaced relation to said wall and over said holes configured for vacuum pressure so that said vacuum force draws said suture into said channel;
   removing said vacuum pressure upon the completion of winding said suture in said channel;
   closing said flaps over said channel so that said flaps abut said wall; and
   removing said pins.

2. The method of claim 1 wherein said package has an oval shape and said winding step further comprises placing said sutures in said channel so that said sutures are arranged in an oval configuration.

* * * * *